(12) United States Patent
Biedermann et al.

(10) Patent No.: US 9,277,942 B2
(45) Date of Patent: Mar. 8, 2016

(54) POLYAXIAL BONE ANCHORING DEVICE WITH ENLARGED PIVOT ANGLE

(71) Applicant: Biedermann Technologies GmbH & Co. KG, Donaueschingen (DE)

(72) Inventors: Lutz Biedermann, VS-Villingen (DE); Wilfried Matthis, Weisweil (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 301 days.

(21) Appl. No.: 13/948,700

(22) Filed: Jul. 23, 2013

(65) Prior Publication Data
US 2014/0031880 A1 Jan. 30, 2014

Related U.S. Application Data

(60) Provisional application No. 61/676,485, filed on Jul. 27, 2012.

(30) Foreign Application Priority Data

Jul. 27, 2012 (EP) .................................... 12178289

(51) Int. Cl.
*A61B 17/86* (2006.01)
*A61B 17/70* (2006.01)

(52) U.S. Cl.
CPC ......... *A61B 17/7037* (2013.01); *A61B 17/7035* (2013.01); *A61B 17/7038* (2013.01); *A61B 17/8605* (2013.01)

(58) Field of Classification Search
CPC ........... A61B 17/7035; A61B 17/7037; A61B 17/8605; A61B 17/7038
See application file for complete search history.

(56) References Cited

U.S. PATENT DOCUMENTS 5,429,639 A * 7/1995 Judet .................. A61B 17/7005 403/362
5,584,834 A * 12/1996 Errico ................ A61B 17/7037 606/264

(Continued)

FOREIGN PATENT DOCUMENTS

EP 2 022 423 A1 2/2009
WO WO 2012/162550 A1 11/2012

OTHER PUBLICATIONS

Extended European Search Report for European Application No. 12178289.0, European Search Report dated Nov. 20, 2012 and mailed Dec. 6, 2012 (7 pgs).

*Primary Examiner* — Christian Sevilla
(74) *Attorney, Agent, or Firm* — Lewis Roca Rothgerber Christie LLP (57) ABSTRACT

A polyaxial bone anchoring device includes a receiving part to receive a rod for coupling the rod to a bone anchoring element, the receiving part having a top end and a bottom end, a first passage at the bottom end with a first longitudinal axis, and a second passage at the top end with a second longitudinal axis that intersects the first longitudinal axis, and a compression element, wherein at least one of the receiving part or the compression element has a seat with an opening facing the bottom end, and wherein the compression element is movable relative to the receiving part along the first longitudinal axis between a first position wherein the seat is expandable and configured for insertion of a head of a bone anchoring element and pivoting of the head, and a second position wherein the seat is compressed to lock an inserted head therein.

26 Claims, 11 Drawing Sheets

(56) References Cited

U.S. PATENT DOCUMENTS

| | | | | |
|---|---|---|---|---|
| 5,797,911 A * | 8/1998 | Sherman | A61B 17/7037 | 606/266 |
| 5,882,350 A * | 3/1999 | Ralph | A61B 17/7032 | 606/278 |
| 6,280,442 B1 * | 8/2001 | Barker | A61B 17/7037 | 606/256 |
| 6,736,820 B2 * | 5/2004 | Biedermann | A61B 17/7037 | 606/308 |
| 6,974,460 B2 * | 12/2005 | Carbone | A61B 17/7034 | 606/270 |
| 7,081,116 B1 * | 7/2006 | Carly | A61B 17/7037 | 606/264 |
| 2002/0091386 A1 * | 7/2002 | Martin | A61B 17/7037 | 606/278 |
| 2003/0055426 A1 * | 3/2003 | Carbone | A61B 17/7034 | 606/271 |
| 2004/0102781 A1 * | 5/2004 | Jeon | A61B 17/7032 | 606/916 |
| 2005/0038430 A1 * | 2/2005 | McKinley | A61B 17/7049 | 606/264 |
| 2005/0080415 A1 * | 4/2005 | Keyer | A61B 17/7038 | 606/278 |
| 2006/0229615 A1 * | 10/2006 | Abdou | A61B 17/8685 | 606/256 |
| 2006/0264933 A1 * | 11/2006 | Baker | A61B 17/7032 | 74/1 R |
| 2006/0293659 A1 * | 12/2006 | Alvarez | A61B 17/7037 | 606/305 |
| 2007/0265621 A1 * | 11/2007 | Matthis | A61B 17/7032 | 606/60 |
| 2008/0161859 A1 * | 7/2008 | Nilsson | A61B 17/7032 | 606/266 |
| 2008/0177322 A1 * | 7/2008 | Davis | A61B 17/7038 | 606/266 |
| 2010/0168800 A1 * | 7/2010 | Biedermann | A61B 17/7037 | 606/302 |
| 2011/0040338 A1 * | 2/2011 | Jackson | A61B 17/8605 | 606/305 |
| 2011/0276098 A1 | 11/2011 | Biedermann et al. | | |
| 2012/0123477 A1 * | 5/2012 | Landry | A61B 17/1604 | 606/264 |
| 2012/0303063 A1 * | 11/2012 | Cahill | A61B 17/7032 | 606/270 |
| 2013/0218213 A1 * | 8/2013 | Lemoine | A61B 17/7032 | 606/305 |
| 2014/0031880 A1 * | 1/2014 | Biedermann | A61B 17/8605 | 606/305 |
| 2014/0142633 A1 * | 5/2014 | Jackson | A61B 17/7032 | 606/273 |

* cited by examiner

POLYAXIAL BONE ANCHORING DEVICE WITH ENLARGED PIVOT ANGLE

CROSS-REFERENCE TO RELATED APPLICATION(S)

The present application claims priority to and the benefit of U.S. Provisional Patent Application Ser. No. 61/676,485, filed Jul. 27, 2012, the contents of which are hereby incorporated by reference in their entirety, and claims priority from European Patent Application EP 12 178 289.0, filed Jul. 27, 2012, the contents of which are hereby incorporated by reference in their entirety.

BACKGROUND

1. Field of the Invention

The invention relates to a polyaxial bone anchoring device providing a pivot angle that is enlarged to one side compared to an opposite side. The polyaxial bone anchoring device comprises a bone anchoring element with a head and a shank and a receiving part for receiving a rod for coupling the rod to the bone anchoring element. The receiving part has two passages, each coaxial with a longitudinal axis, wherein the longitudinal axes of the two passages intersect one another and wherein one of the passages includes a seat configured to allow pivoting of the head. The head is insertable into the seat from a bottom end of the receiving part.

2. Description of Related Art

A polyaxial bone anchoring device with an enlarged pivot angle to one side is known from U.S. Pat. No. 6,736,820 B2. This bone anchoring device comprises a screw member that is pivotably held in a receiving part, wherein the receiving part has an open first bore and a second bore on the end opposite to the first bore. On the bottom of the first bore, a seat for the head is provided. In order that the screw member can be pivoted to at least one side by an enlarged angle, an edge bounding the free end of the second bore viewed relative to the axis of the first bore is of asymmetric construction. The diameter of the second bore is greater than that of a threaded section of the screw member and smaller than that of the head.

Another bone anchoring device with an enlarged pivot angle is known from U.S. Pat. No. 6,974,460 B2. It includes a coupling element having an inner surface defining a first bore coaxial with a first longitudinal axis, and a second bore coaxial with a second longitudinal axis, whereby the second longitudinal axis intersects the first longitudinal axis. The coupling element has a seat adjacent to the lower end of the coupling element for the head of a bone anchoring element.

The polyaxial bone anchoring devices described above are top-loading anchoring devices wherein the anchoring element is inserted into the receiving part from an upper end thereof.

A bottom-loading polyaxial bone anchoring device is known from US 2011/0276098 A1. This polyaxial anchoring device comprises a rod receiving portion and a head receiving portion and an outer locking ring that is configured to compress the head receiving portion to clamp and finally lock the head. The anchoring element is insertable into the receiving part from a bottom end of the receiving part.

SUMMARY

It is the object of the invention to provide a polyaxial bone anchoring device that provides for enlarged angulation and that provides for an increased variety of applications.

A polyaxial bone anchoring device according to embodiments of the invention is a bottom loading polyaxial bone anchoring device, wherein the anchoring element can be inserted into a receiving part from a bottom end of the receiving part. This allows for providing a modular system. In one embodiment, the bone anchoring device may be delivered by a manufacturer as a receiving part pre-assembled with an inner compression member, and separate therefrom, one or a plurality of different bone anchoring elements. In another embodiment, the bone anchoring device may be delivered by a manufacturer as a receiving part pre-assembled with an outer locking ring and also separate therefrom one or a plurality of bone anchoring elements. By means of this, various bone anchoring elements with shanks having different diameters, thread forms and/or various other different features can be combined with a receiving part according to actual clinical requirements in a particular clinical situation. This gives a surgeon or other practitioner a more diverse or wider choice of implants.

In addition, due to such modularity, the costs of stockholding can be decreased.

The polyaxial bone anchoring device provides for an enlarged pivot angle to one side compared to an opposite side, i.e. has a favored angle design. A pull-out force that is necessary to pull out the bone anchoring element through an opening at the bottom end of the receiving part is comparable to or at least not less than a pull-out force of comparable polyaxial bone anchoring devices that do not have a favored angle design. This renders the bone anchoring device particularly suitable for applications of lateral mass fixation, for example, at the cervical spine.

The polyaxial bone anchoring device does not require additional parts compared to anchoring devices without a favored angle design. Hence, the polyaxial bone anchoring device provides for reduced dimensions in terms of height as well as in terms of diameter, which makes it particularly suitable for applications where small-sized anchoring devices are required, such as in the fields of cervical spine surgery or pediatric applications, trauma, and minimally open or minimally invasive applications for bone surgery.

BRIEF DESCRIPTION OF THE DRAWINGS

Further features and advantages will become apparent from the description of embodiments by means of accompanying drawings. In the drawings.

DETAILED DESCRIPTION

Figures 1, 2:
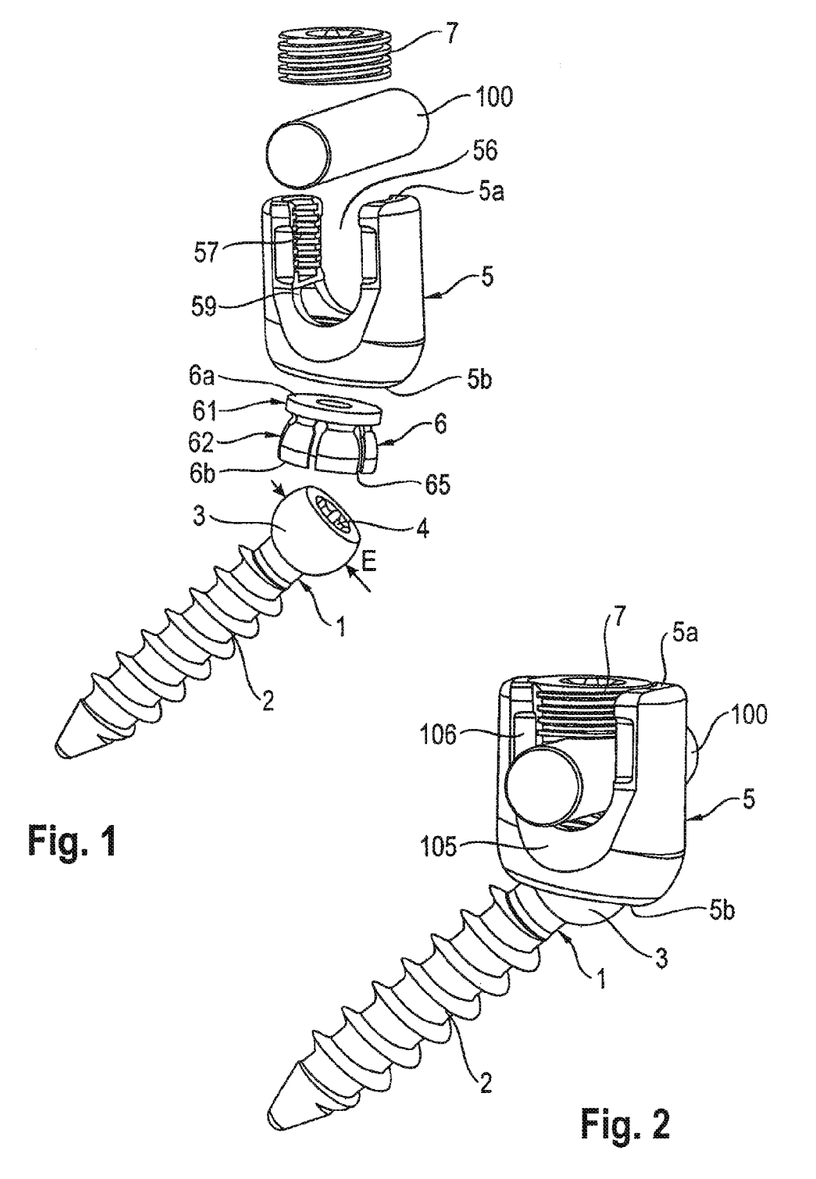
FIG. 1 shows an exploded perspective view of a polyaxial bone anchoring device according to a first embodiment.
FIG. 2 shows a perspective view of the polyaxial bone anchoring device of FIG. 1 in an assembled state.
Figure 3:
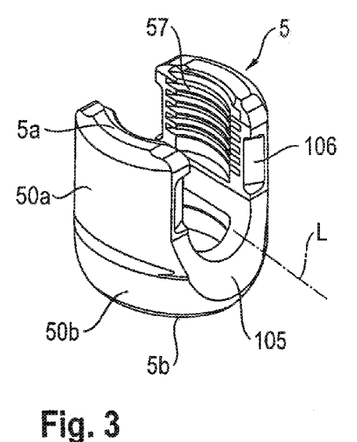
FIG. 3 shows a perspective view of the receiving part of the polyaxial bone anchoring device of FIG. 1.
Figure 4:
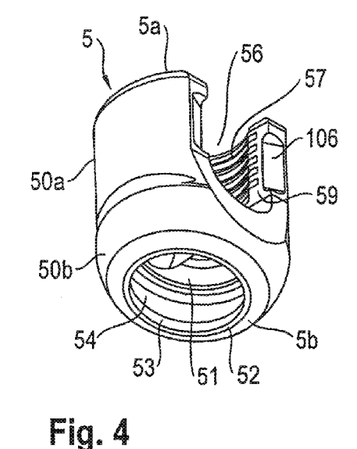
FIG. 4 shows another perspective view from the bottom of the receiving part of FIG. 3.
Figure 5:
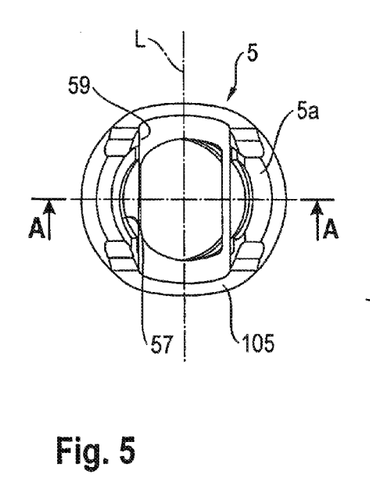
FIG. 5 shows a top view of the receiving part of FIG. 3.

As shown in FIGS. 1 and 2, a polyaxial bone anchoring device according to a first embodiment includes a bone anchoring element 1 in the form of a bone screw having a threaded shank 2 and a spherical segment-shaped head 3. The head 3 has a recess 4 for engagement with a tool. The spherical segment-shaped head 3 may comprise a section including a largest diameter E of the head 3. The bone anchoring device further includes a receiving part 5 for receiving a rod 100 to connect the rod 100 to the bone anchoring element 1. In the receiving part 5, a compression member 6 for exerting pressure onto the head 3 is arranged. Furthermore, a locking element, in the form of, for example, an inner screw 7 is provided for securing and fixing the rod 100 and for locking the head 3 in the receiving part 5.

Referring further to FIGS. 3 to 6, the receiving part 5 has a top end 5a and a bottom end 5b. An outer surface of the receiving part is substantially cylindrical adjacent to the top end 5a and extends to a tapering surface portion 50b adjacent to the bottom end 5b. A first passage 51 that is coaxial with a first longitudinal axis 51a extends from the bottom end 5b toward the top end 5a. A second passage 56 coaxial with a second longitudinal axis 56a extends from the top end 5a toward the bottom end 5b. As can be seen in particular in FIGS. 5 and 6, the first passage 51 and the second passage 56 are in communication with one another. The first longitudinal axis 51a and the second longitudinal axis 56a include an angle α with one another and intersect at a point in the interior of the receiving part 5. By means of this design, the bottom end 5b defines a first plane 51b and the top end 5a defines a second plane 56b, wherein the first plane 51b and the second plane 56b intersect. The angle α included by the first longitudinal axis 51a and the second longitudinal axis 56a may be between around 5° and around 20°, for example, approximately 15°.

Figure 6:
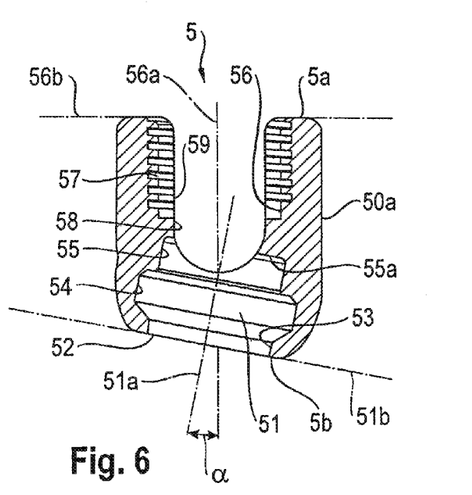
FIG. 6 shows a cross-sectional view of the receiving part along line A-A in FIG. 5.
Figure 7:
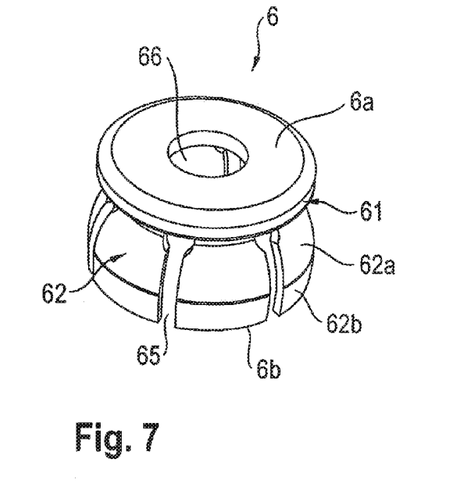
FIG. 7 shows a perspective view from the top of a compression member of the polyaxial bone anchoring device according to the first embodiment.
Figure 8:
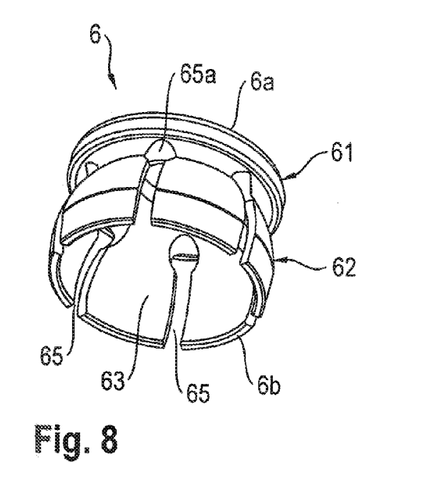
FIG. 8 shows another perspective view from the bottom of the compression member of FIG. 7.
Figure 9:
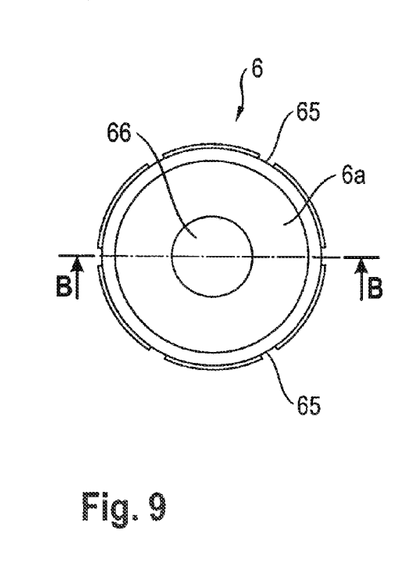
FIG. 9 shows a top view of the compression member of FIG. 7.
Figure 10:
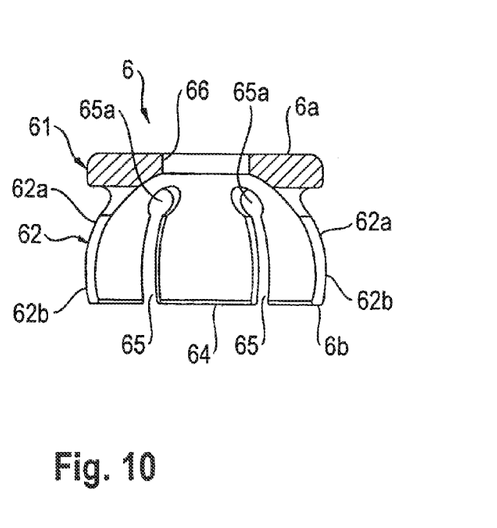
FIG. 10 shows a cross-sectional view of the compression member along line B-B in FIG. 9.

The passages are now described in more detail. The first passage 51 provides for an opening 52 at the bottom end 5b, wherein a diameter of the opening 52 is greater than the greatest diameter E of the head 3. Adjacent to the bottom end 5b the first passage 51 comprises a tapered section 53 that narrows toward the bottom end 5b. Following the tapered section 53 an enlarged section 54 is provided with an inner diameter that is greater than an inner diameter of the tapered section 53 and that provides a space so that the compression member 6 can expand therein. Following the enlarged section 54, there is a cylindrical section 55 with a smaller diameter compared to the enlarged section 54, the end of which provides for a stop 55a that limits an upward movement of the compression member 6.

The second passage 56 comprises adjacent to the top end 5a a section 57 with an internal thread that operates with the thread of the inner screw 7. Following the threaded section 57, there is a section 58 with a reduced inner diameter compared to the section 57 and the cylindrical section 55 of the first passage, thereby providing the stop 55a. Furthermore, adjacent to the top end 5a, a substantially U-shaped recess 59 is provided that extends into the direction of the bottom end 5b. By means of the U-shaped recess 59, a channel for receiving the rod 100 is provided. The channel axis L extends perpendicular to the second longitudinal axis 56a.

The receiving part 5 may further have inclined cuts 105 on either end of the channel formed by the U-shaped recess 59 that reduce the outer diameter of the receiving part 5 in a direction of the channel axis L. Furthermore, tool engagement recesses 106 may be provided on either end of the channel and on both sidewalls of the channel. The channel axis L and the second longitudinal axis 56a define a plane. The first longitudinal axis 51a extends at an angle relative to that plane, i.e. intersects the plane. Therefore, an asymmetry in view of the pivot angle of the bone anchoring element is provided transverse to the channel L, which is transverse to the rod axis.

Referring further to FIGS. 7 to 10, the compression member 6 has a top end 6a and a bottom end 6b. Adjacent to the top end 6a, there is a substantially cylindrical portion 61 with a flat surface at the top end 6a and with an outer diameter that is only slightly smaller than an inner diameter of the section 55 of the first passage 51 so that the cylindrical section 61 fits into the cylindrical section 55 of the passage and can move therein in axial direction of the first longitudinal axis 51a.

Following the cylindrical portion 61, the compression member 6 has a cap-like portion 62 that is recessed with respect to the cylindrical portion 61 at a position adjacent to the cylindrical portion 61. The cap-like portion 62 defines a hollow interior 63 forming a seat for the head 3 of the bone anchoring element 1. The hollow interior 63 is substantially spherically-shaped mating the spherical shape of the head 3. The second end 6b of the compression member has an opening 64 for the insertion of the head 3. An outer wall of the cap-like portion 62 comprises a first section 62a that is spherical and a second section 62b adjacent to the opening 64 that is tapered. The tapered section 62b of the compression member 6 cooperates with the tapered section 53 of the first passage 51 of the receiving part 5. The cap-like portion 62 of the compression member further comprises a plurality of slits 65 extending from an edge of the opening 64 through the cap-like portion up to a distance from the cylindrical portion 61. The respective ends 65a of the slits may have the shape of a section of a circle or may be otherwise enlarged with respect to the dimension of the slits 65 to facilitate a radial expansion or compression of the compression member. The dimension of the hollow interior 63, the number and dimensions of the slits 65 are such that the wall of the cap-like portion 62 is flexible enough to snap onto the head 3 when the head 3 is being inserted. The seat provided by the cap-like portion 62 of the compression member 6 allows pivoting of the head 3 in a symmetrical fashion relative to a central axis of the compression member 6.

A maximum outer diameter of the cap-like portion 62 can be slightly larger than the inner diameter of the lower opening 52 of the receiving part 5 at the bottom end 5b, because the cap-like section 62 can be compressed during insertion of the compression member 6 into the first passage 51 through the lower opening 52. A length in axial direction of the compression member 6 is such that when the compression member 6 is inserted into the first passage 51 of the receiving part 5 and when it abuts with the top end 6a against the stop 55a of the receiving part 5, the second end 6b is located above the tapered section 53 of the first passage 51 of the receiving part (FIGS. 13 and 14) to allow a radial expansion of the cap-like portion 62. Because the compression member 6 is symmetric with respect to the pivoting of the head 3, securing of the compression member 6 against rotation is not necessary.

The compression member 6 further comprises a coaxial bore 66 for providing access to the screw head 3 by a tool.

The inner screw 7 has a thread corresponding to the internal thread provided in the second passage 56. Preferably, a thread form that prevents the walls of the channel from splaying is used. Such a thread form can be, for example, a flat thread, a negative angle thread or a saw-tooth thread.

All parts described before may be made of a bio-compatible material, such as a bio-compatible metal like stainless steel or titanium, or a bio-compatible metal alloy, for example, Nitinol, or are made of a bio-compatible plastic material, for example, polyetheretherketone (PEEK). The parts may be of the same or of different materials.

Figure 11:
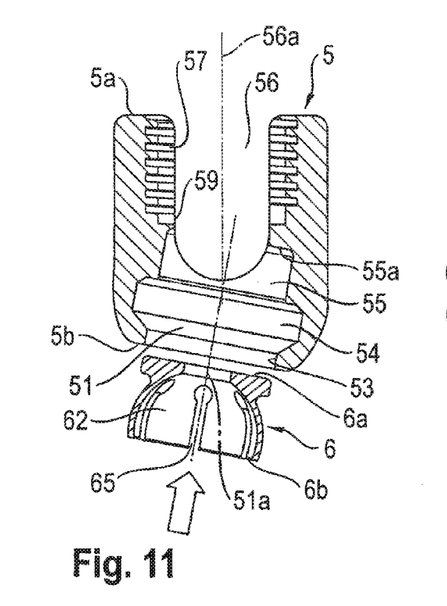
FIGS. 11 to 14 show cross-sectional views of steps of mounting the compression member and the bone anchoring element to the receiving part according to the first embodiment, the section taken along line A-A in FIG. 5.
Figure 12:
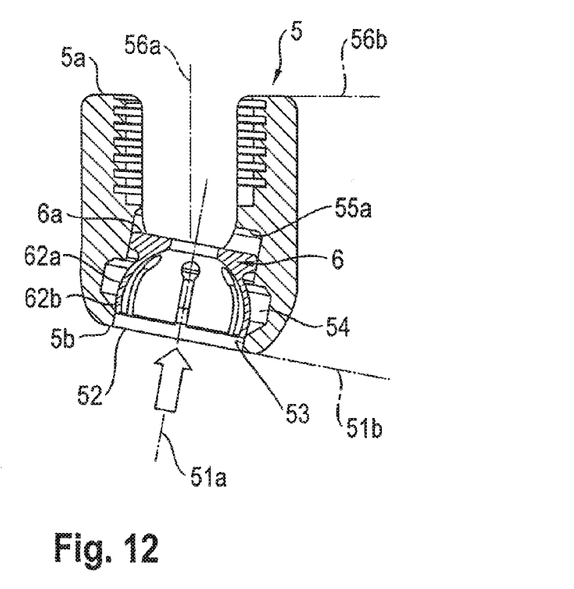

The steps of assembling the bone anchoring device are now explained with respect to FIGS. 11 to 14. First, as shown in FIGS. 11 and 12, the compression member 6 is introduced from the bottom end 5b through the opening 52 into the first passage 51 of the receiving part 5. When the cap-like portion 62 of the compression member 6 passes the tapered section 53 of the first passage 57, it is slightly compressed. The compression member is further moved upward in the first passage 51 toward the first end 5a of the receiving part 5 until it abuts against the stop 55a of the cylindrical section 55. In this position, the bottom end 6b of the compression member 6 is above the tapered section 53 of the first passage 51 and is located in the enlarged section 54 that provides space for a radial expansion of the cap-like portion 62.

Figure 13:
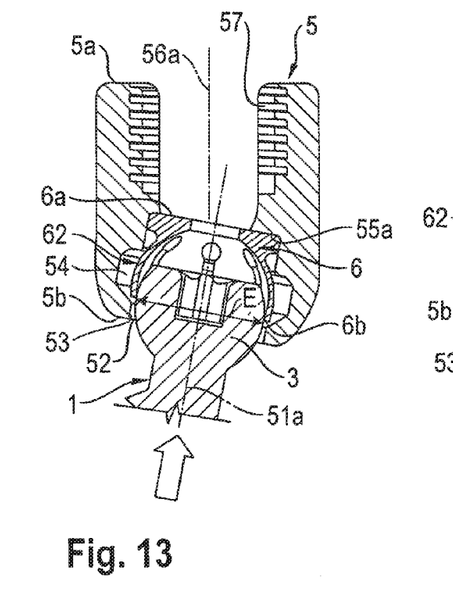
Figure 14:
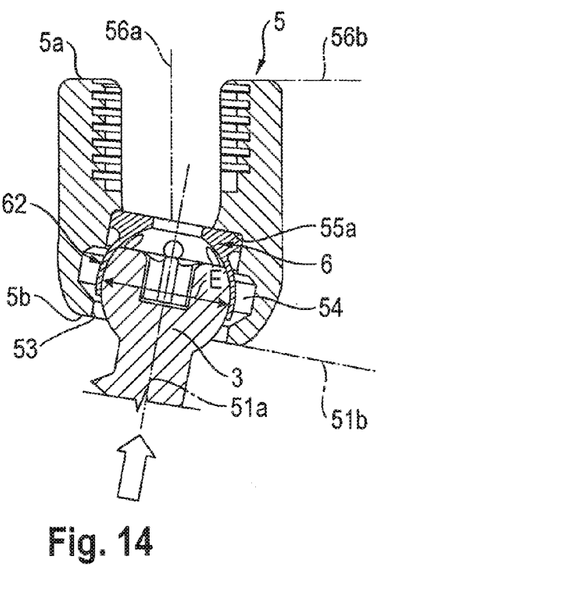

When the compression member 6 is in its uppermost position at the stop 55a, the head 3 of the bone anchoring element 1 is inserted into the first passage 51 of the receiving part 5 through the lower opening 52 at the bottom end 5b. When the head 3 enters into the hollow interior 63 through the lower opening 64 of the compression member 6, the cap-like portion 62 expands radially thereby permitting the insertion of the head 3, as shown in FIG. 13. When the head 3 has entered the hollow interior 63, the tapered outer surface section 62b of the cap-like portion 62 encompasses the head 3 at its greatest diameter E.

The use of the polyaxial bone anchoring device is now described with reference to FIGS. 15 and 16. The receiving part 5 may be delivered in a pre-assembled manner with the compression member 6 inserted into the first passage 51. After assembling the head 3 of the anchoring element 1 with the receiving part 5, the anchoring element 1 is inserted into a bone part or a vertebra. Typically, at least two bone anchoring devices are used that are connected with a rod 100. After insertion of the anchoring elements into the bone or into vertebrae, the receiving parts 5 are aligned to allow the insertion of the rod 100 by pivoting them with respect to the bone anchoring elements 1. The angular position may be held in a preliminary manner by friction between the head 3 and the cap-like portion 62, when the compression member 6 is moved downward so that its outer tapered section 62b engages the tapered section 53 of the first passage 51. After insertion of the rod 100, the inner screw 7 is inserted and tightened thereby moving the compression member 6 further downward so that it is compressed around the head 3 to lock the head 3 and the rod 100.

Figure 15:
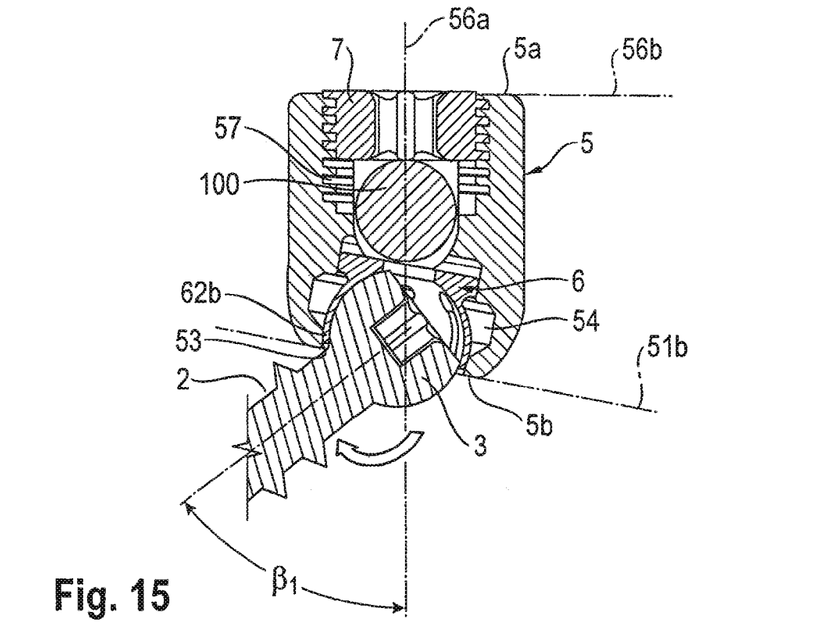
FIG. 15 shows a cross-sectional view of the polyaxial bone anchoring device in an assembled state, the section taken along line A-A of the receiving part shown in FIG. 5, wherein the bone anchoring element and the receiving part are pivoted relative to one another with a maximum pivot angle in a first direction.

As can be seen in FIG. 15, in the assembled state, there is a first maximum pivot angle $\beta_1$ relative to the second longitudinal axis 56a, which is defined by the abutment of the shank 2 of the bone anchoring element 1 against the lower end 5b of the receiving part in one direction.

Figure 16:
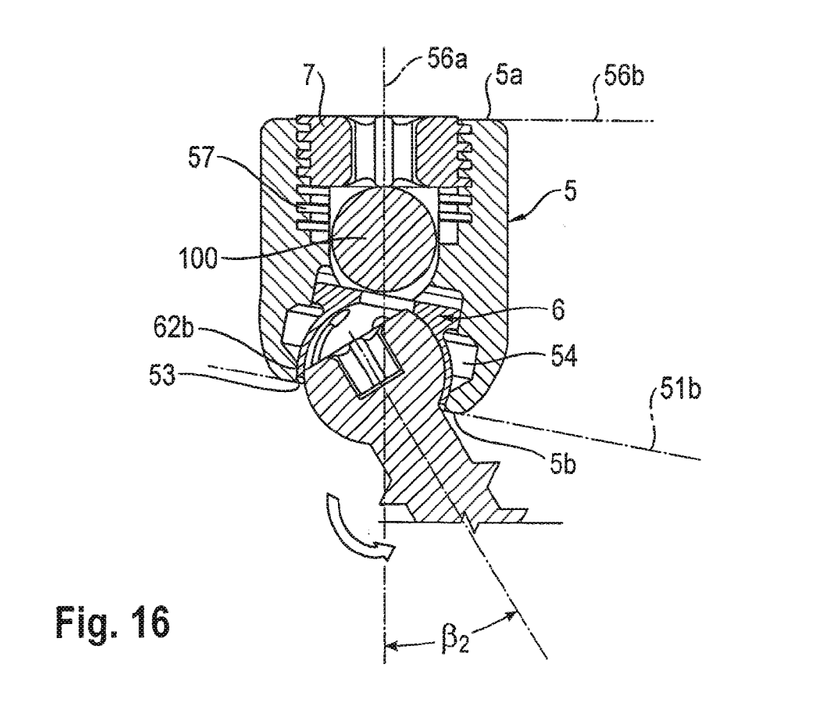
FIG. 16 shows a cross-sectional view of the polyaxial bone anchoring device in an assembled state, the section taken along line A-A of the receiving part shown in FIG. 5, wherein the bone anchoring element and the receiving part are pivoted relative to one another with a maximum pivot angle in a second direction opposite to the first direction.
Figure 17:
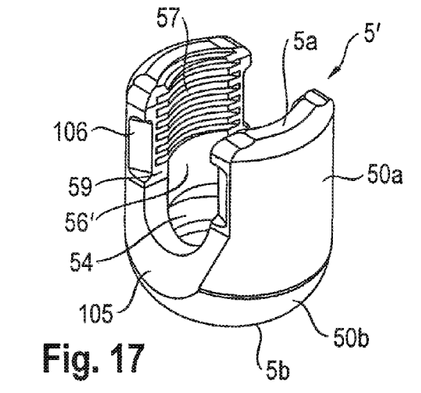
FIG. 17 shows a perspective view of a receiving part according to a modified first embodiment.
Figure 18:
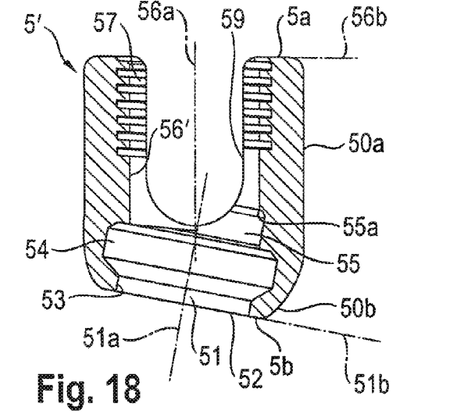
FIG. 18 shows a cross-sectional view of the receiving part of FIG. 17, the section taken in a plane perpendicular to the rod axis and going through the middle of a channel for the rod.

As can be seen in FIG. 16, a second maximum pivot angle $\beta_2$ relative to the second longitudinal axis 56a is defined by the abutment of the shank 2 against the lower end 5b in an opposite direction. The first maximum pivot angle $\beta_1$ is greater than the second maximum pivot angle $\beta_2$. While the pivoting of the bone anchoring element 1 relative to the receiving part 5 is symmetrical relative to the first longitudinal axis 51a, the pivoting is asymmetrical relative to the second longitudinal axis 56a, and is therefore also asymmetrical relative to the channel axis L and the rod 100.

Because the seat for the head 3 provided by the compression member 6 is symmetrical with respect to the pivoting of the head 3, the pull-out force for the head 3 is not decreased compared to comparable polyaxial bone anchoring devices without an enlarged pivot angle.

The polyaxial anchoring device may be particularly useful in applications of cervical spine surgery, wherein enlarged pivot angles only to one side and to an opposite side may be needed.

A modification of the first embodiment of the polyaxial bone anchoring device is shown in FIGS. 17 to 21. The modified first embodiment differs in the shape of the receiving part and is identical or highly similar to the first embodiment in all other parts. The receiving part 5' has a second passage 56' with a diameter greater than the outer diameter of the cylindrical portion 61 of the compression member 6. The second passage 56' extends into the cylindrical section 55 of the first passage 51. Therefore, as can be seen in particular in FIGS. 18 and 19, the inner diameter of the second passage 56' is sized such as to allow the introduction of the compression member 6 from the top end 5a.

Figure 19:
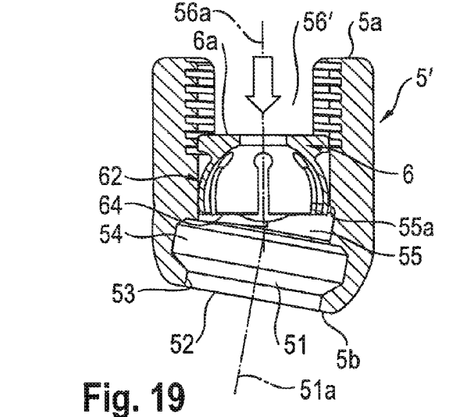
FIGS. 19 to 21 show cross-sectional views of steps of mounting the compression member to the receiving part according to the modified first embodiment.
Figure 20:
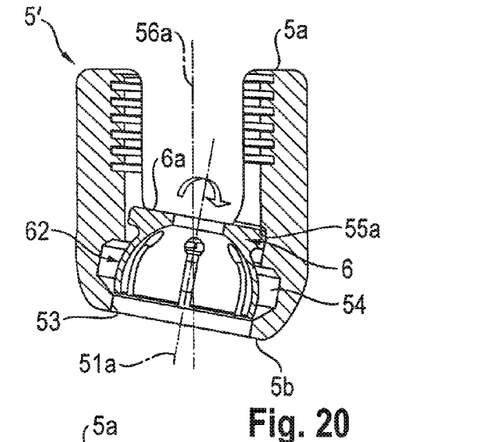
Figure 21:
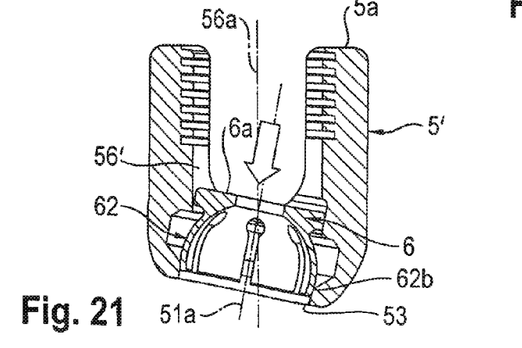

Steps of assembling the receiving part 5' and the inner compression member 6 are shown in FIGS. 19 to 21. As depicted in FIG. 19, the compression member 6 is introduced into the first passage 56' in an orientation in which the opening 64 shows toward the bottom end 5b of the receiving part 5'. When the compression member 6 has reached the cylindrical section 55 of the first passage 51, the compression member 6 is tilted to align it with the first longitudinal axis 51a so that it can engage the cylindrical section 55 of the first passage 51 as can be seen in FIG. 20. As shown in FIG. 21, the compression member 6 can further be moved downward until its tapered outer section 62b engages the tapered section 53 of the receiving part 5'. The other steps are the same as for the first embodiment.

In a still further modified embodiment, a transverse pin (not shown) can be provided in the receiving part that cooperates with the compression member to secure the compression member against tilting once it has reached its position in the first passage.

Alternatively, with the modified first embodiment, the compression member 6 can also be inserted from the bottom end 5b of the receiving part 5'.

Figures 22, 23:
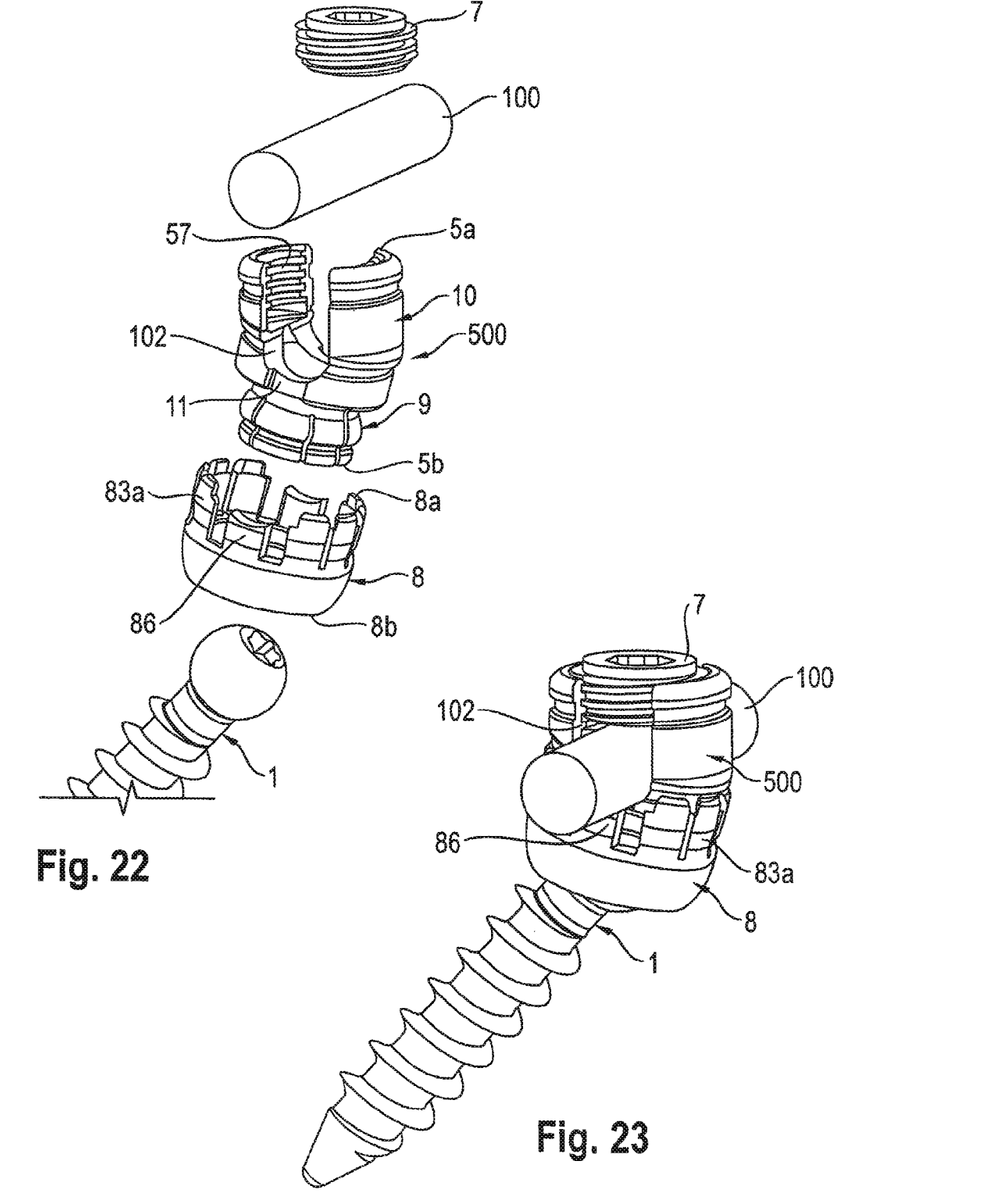
FIG. 22 shows an exploded perspective view of a polyaxial bone anchoring device according to a second embodiment.
FIG. 23 shows a perspective view of the polyaxial bone anchoring device of FIG. 22 in an assembled state.

A second embodiment the polyaxial bone anchoring device is now described with reference to FIGS. 22 to 38. As shown in particular in FIGS. 22 and 23, a polyaxial bone anchoring device according to the second embodiment differs from the polyaxial bone anchoring device according to the first embodiment in that instead of an inner compression member, an outer locking ring 8 is used that is configured to compress a portion of a receiving part 500 to clamp and lock the head 3 therein. All portions of the second embodiment that are identical with the function or the design of corresponding portions of the first embodiment have the same reference numerals and the description thereof will not be repeated.

The receiving part 500 comprises a first portion 9 that is adjacent to the bottom end 5b and a second portion 10 that is adjacent to the top end 5a. The first portion 9 comprises the first passage 51 coaxial with the first longitudinal axis 51a and the second portion 10 comprises the second passage 56 coaxial with the second longitudinal axis 56a. As in the first embodiment, the first and the second longitudinal axes intersect and include an angle α. The plane 51b defined by the bottom end 5b is inclined relative to the plane 56b defined by the top end 5a and therefore, the planes intersect.

At the bottom end 5b, the first portion 9 has an opening 91 the diameter of which is such that the head 3 can be inserted. At a distance from the bottom end 5b, the first passage 51 comprises a head receiving portion 92 having a spherical segment shape that mates the shape of a portion of the head 3. The head receiving portion 92 provides a seat for the head 3 that allows the head 3 to pivot therein. Furthermore, the head receiving portion 92 is configured to encompass the head 3 of the bone anchoring element 1 laterally, thereby covering the largest diameter E of the head 3.

A plurality of slits 93 are provided in the head receiving portion 92 that are open to the second end 5b. The slits 93 render the head receiving portion 92 flexible so that it can be expanded when the head 3 is inserted and can be compressed to clamp and finally lock the head 3 by means of friction. The number and size of the slits 93 is provided depending on the desired flexibility of the head receiving portion 92.

Figures 24, 25, 26, 27:
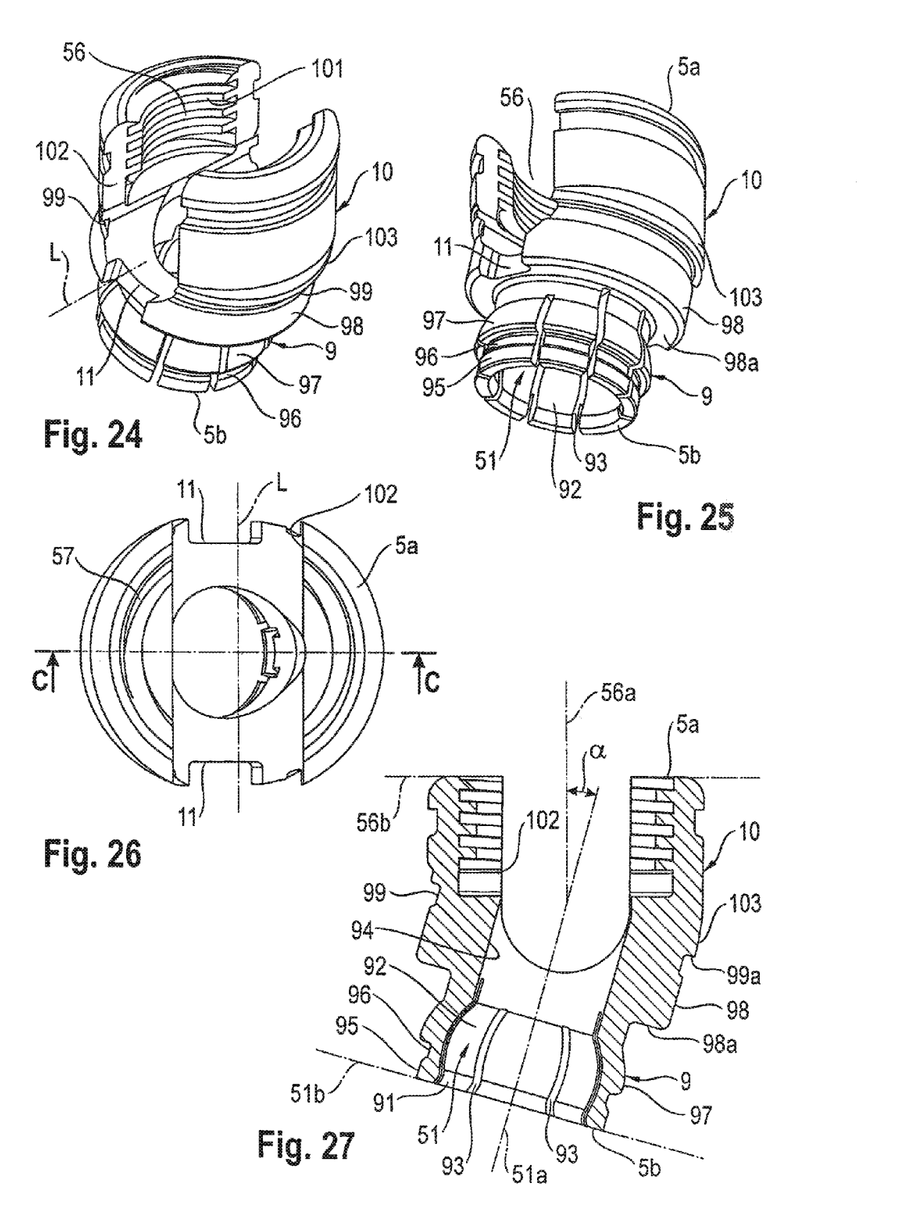
FIG. 24 shows a perspective view of the receiving part of the polyaxial bone anchoring device according to the second embodiment.
FIG. 25 shows another perspective view from the bottom of the receiving part according to the second embodiment.
FIG. 26 shows a top view of the receiving part according to the second embodiment.
FIG. 27 shows a cross-sectional view of the receiving part according to the second embodiment along line C-C in FIG. 26.
Figure 28:
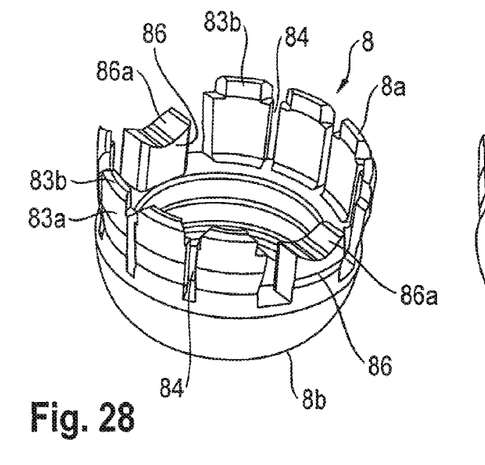
FIG. 28 shows a perspective view of a locking ring of the polyaxial bone anchoring device according to the second embodiment.
Figure 29:
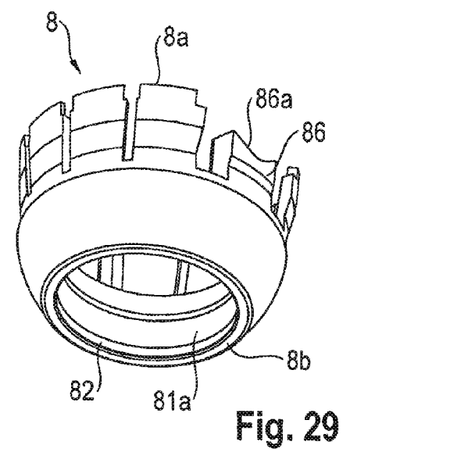
FIG. 29 shows another perspective view from the bottom of the locking ring of FIG. 28.
Figure 30:
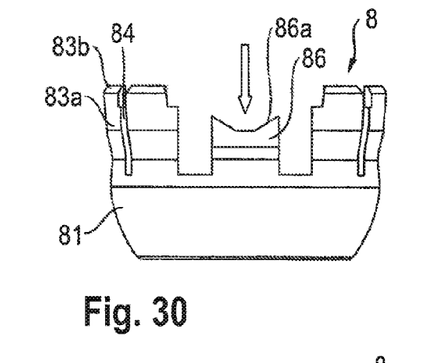
FIG. 30 shows a side view of the locking ring of FIG. 28.
Figure 31:
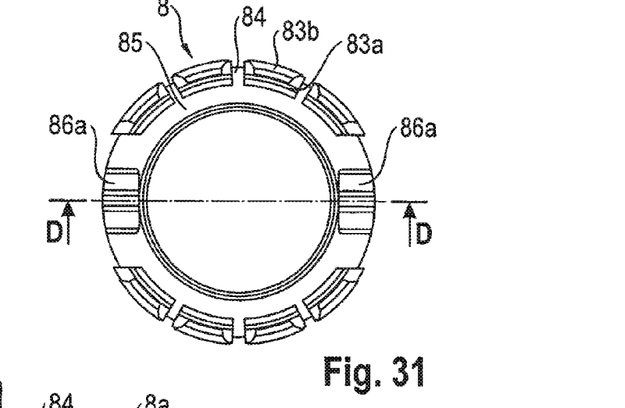
FIG. 31 shows a top view of the locking ring of FIG. 28.
Figure 32:
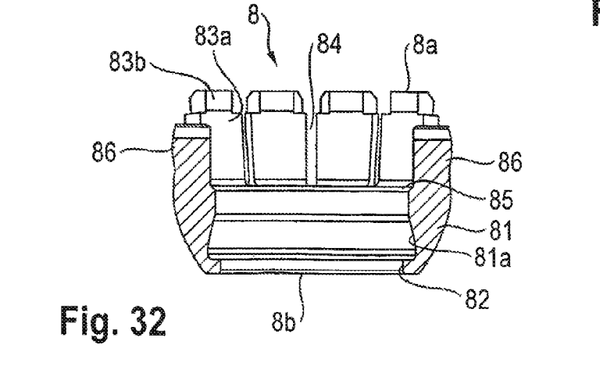
FIG. 32 shows a cross-sectional view of the locking ring along line D-D in FIG. 31.
Figure 33:
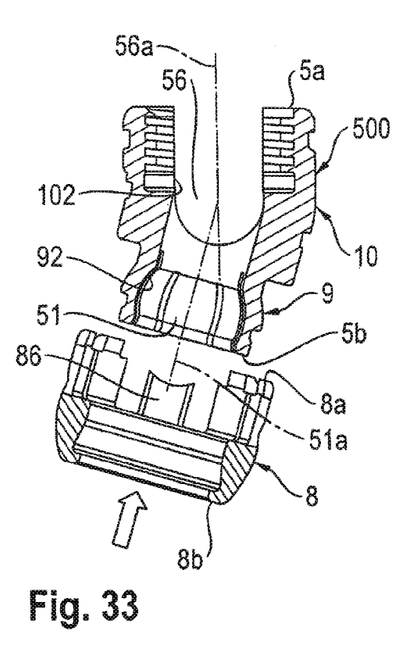
FIGS. 33 to 36 show cross-sectional views of steps of assembling the polyaxial bone anchoring device according to the second embodiment, the section taken along line C-C in FIG. 26.

As can be seen in particular in FIG. 27, the head receiving portion is rotationally symmetrical with respect to the first longitudinal axis 51a. More in detail, when the head 3 is inserted into the head receiving portion 92, it can pivot to a maximum pivot angle in one direction and to the same maximum pivot angle in the opposite direction in relation to the first longitudinal axis 51a.

Following the head receiving portion 92, the first passage 51 further comprises a cylindrical section 94 extending to a distance from the bottom end 5b. At least some of the slits 93 may extend into the cylindrical section 94 to increase the flexibility of the head receiving portion 92.

The outer surface of the first portion 9 of the receiving part 500 comprises several sections. Adjacent to the bottom end 5b there is a cylindrical section 95. Following the cylindrical section 95 there is a circumferentially extending lower groove 96. Adjacent to the lower groove 96 there is an outwardly curved or conically widening section 97, the diameter of which increases toward the bottom end 5b. Adjacent to or at some distance from the outwardly curved section 97 there is a cylindrical section 98 that is symmetrical in relation to the first longitudinal axis 51a. An outer diameter of the cylindrical section 98 is greater than an outer diameter of the outwardly curved section 97. A downward facing surface of the cylindrical section 98 forms a stop 98a for the locking ring 8. Adjacent to the cylindrical section 98, a circumferentially extending upper groove 99 is provided for engagement with a portion of the locking ring 8. The upper groove 99 has an upper wall providing a stop 99a for the locking ring 8.

The second portion 10 of the receiving part 500 comprises the second passage 56 that consists of a internally threaded section 101 adjacent to the top end 5a. Furthermore, the second portion 10 comprises a substantially U-shaped recess 102 extending from the top end 5a toward the bottom end 5b into the first passage 51. Hence, the bottom of the U-shaped recess 102 reaches into the hollow cylindrical section 94 of the first passage 51.

An outer surface of the second portion 10 is substantially cylindrical and may continue in a small tapered section 103 at the transition between the second portion 10 and the first portion 9. Further, as can be seen in FIGS. 24 to 26 cut-outs 11 are provided in the cylindrical section 98 of the first portion 9 on either end of the channel formed by the U-shaped recess 102.

The locking ring 8 is now described referring to FIGS. 28 to 32. The locking ring 8 has an upper end 8a and a lower end 8b. In the mounted state, the upper end 8a is oriented in the direction of the top end 5a of receiving part 500, while the lower end 8b is oriented toward the bottom end 5b of the receiving part 500. Near the lower end 8b, a first portion 81 with an inner surface 81a is provided that cooperates with the outwardly curved section 97 of the receiving part 500 to compress the head receiving portion 92. The outer surface of the first portion 81 may also be tapered to reduce an outer bottom diameter. The size of the first portion 81 is such that, for example, the tapered inner surface 81a can engage the outwardly curved section 97 of the head receiving portion 92 to exert a compression force onto the head receiving portion 92. The inner surface 81*a* of the first portion 81 of the locking ring 8 can also be curved with a curvature directed toward a center of the locking ring 8.

At the lower end 8*h*, the locking ring 8 includes an inwardly projecting edge 82, an inner diameter of which is smaller than an inner diameter of the other portions of the locking ring 8. The inwardly projecting edge 82 is configured to engage the lower groove 96 of the receiving part 500.

The locking ring 8 further has upwardly extending wall portions 83*a* that are separated from each other by slits 84. The upwardly extending wall portions 83*a* are arranged at an outer circumference of an inner circumferential shoulder 85 of the locking ring 8, and render the upper portion of the locking ring flexible. The number and size of the slits and the thickness of the wall portions 83*a* are configured such that a desired flexibility is realized. At the free ends of the wall portions 83*a* engagement sections 83*b* are provided that are shaped so as to engage the upper groove 99 provided on the outer surface of the receiving part 500.

Figure 34:
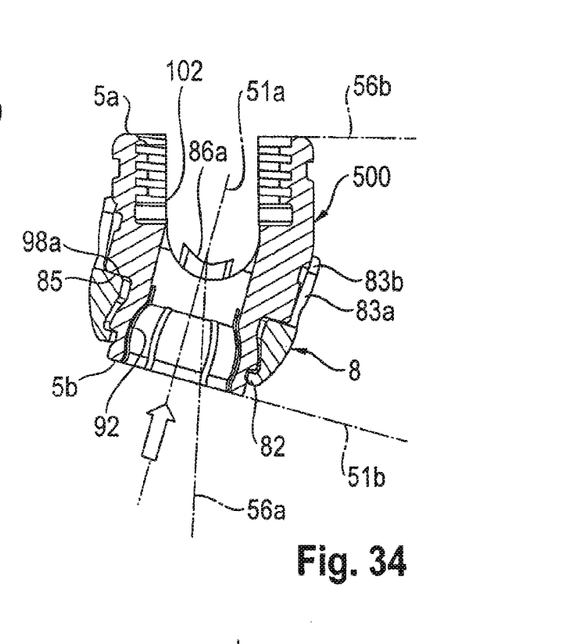

The locking ring 8 is sized in such a way with respect to the first portion 9 of the receiving part 500, that the head receiving portion 92 can expand within the locking ring 8 to allow the insertion of the head 3 when the locking ring 8 is in the first position as shown in FIG. 34.

Figure 35:
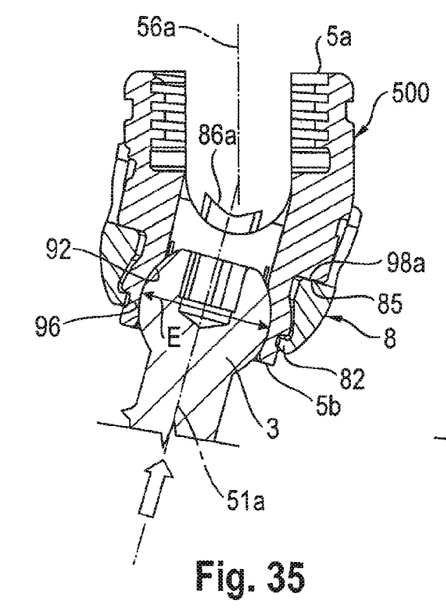

Two projections 86 that are located diametrically opposite to each other, are formed between the flexible wall portions 83*a* of the locking ring 8. The projections 86 have a height where they extend into the cut-outs 11 and project above the bottom of the U-shaped recess 102, when the locking ring 8 is in a position in which the head 3 is not yet locked as shown in FIGS. 34 and 35. A free end surface 86*a* of the projections 86 is concave. For example, the free end surface 86*a* can be substantially V-shaped to provide two lines of contact with the rod 100.

The locking ring 8 is arranged in such a manner around the first portion 9 of the receiving part 500 that the projections 86 are located at positions of (e.g., are aligned with) the U-shaped recess 102. In this case, the projections 86 prevent the locking ring 8 from rotating when the rod 100 is not inserted.

The flexibility of the head receiving portion 92 and the size of the head receiving portion allows for assembling the locking ring 8 from the bottom end 5*b* onto the first portion 9.

Steps of assembling the polyaxial bone anchoring device are described with reference to FIGS. 33 to 36. In a first step, shown in FIG. 33, the locking ring 8 is mounted onto the first portion 9 of the receiving part 500 from the bottom end 5*b* with its flexible wall portions 83*a* oriented toward the top end 5*a*. When mounting the locking ring 8, the head receiving portion 92 is slightly compressed. As shown in FIG. 34, the locking ring 8 is moved upward until its circumferential shoulder 85 abuts against the lower surface 98*a* of the cylindrical outer surface section 98 of the first portion 9. The flexible wall portions 83*a* are not in engagement with the upper groove 99. The projections 86 extend into the cut-outs 11 and project over the bottom of the U-shaped recess 102. The locking ring 8 is held in a preliminary manner in this position because the inwardly projecting edge 82 engages the lower groove 96.

As shown in FIG. 35, the head 3 of the bone anchoring element 1 can be inserted into the head receiving portion 92 of the first portion 9 when the locking ring 8 is in the position described before.

In a next step (not shown), the locking ring 8 may be moved downward toward the bottom end 5*b* until its flexible wall portions 83*a* resiliently snap into the upper groove 99. Once in this position, the free upper edge of the engagement portions 83*b* abut against the stop 99*a* of the groove 99, thereby preventing upward movement of the locking ring 8 out of this position. In this configuration, the head 3 is prevented from removal through the lower opening 91. Furthermore, in this configuration, the head 3 may be clamped by friction so that a certain angular position may be maintained in a preliminary manner.

Figure 36:
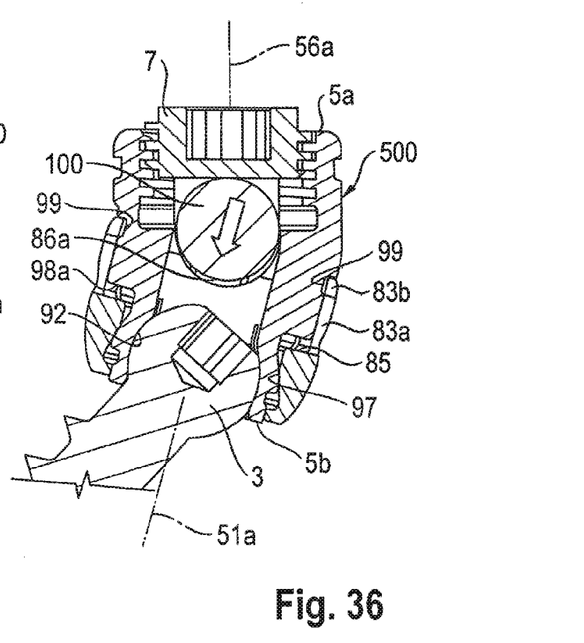

In a next step, as shown in FIG. 36, the rod 100 is inserted into the channel from the top end 5*a* until it abuts against the free surface 86*a* of the projections 86. Because the first and second longitudinal axes are tilted with respect to one another, the engagement of the rod 100 with the free end surface 86*a* is slightly asymmetric. If the free end surface 86*a* provides for a contact along two lines, for example with a V-shaped cross-section, a safe contact can be achieved even in such asymmetric engagement condition.

Once the inner screw 7 is inserted into the receiving part 500 and tightened, the force exerted by the rod 100 onto the projections 86 of the locking ring 8 move the locking ring 8 downward into a final position in which the head receiving portion 92 is compressed so as to lock the head 3.

Figure 37:
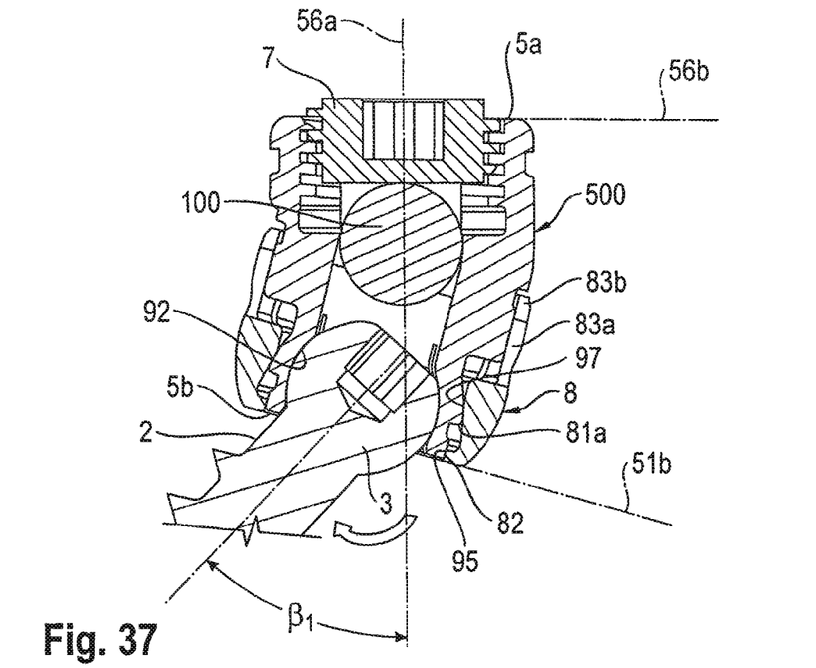
FIG. 37 shows a cross-sectional view of the polyaxial bone anchoring device according to the second embodiment in an assembled state, wherein the bone anchoring element and the receiving part are pivoted relative to one another with a maximum pivot angle in a first direction.
Figure 38:
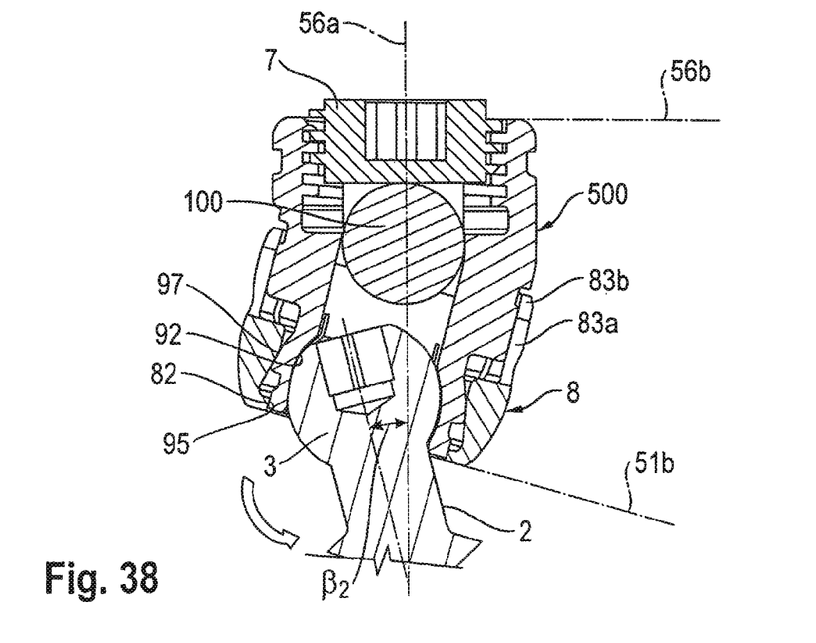
FIG. 38 shows a cross-sectional view of the polyaxial bone anchoring device according to the second embodiment in an assembled state, wherein the bone anchoring element and the receiving part are pivoted relative to one another with a maximum pivot angle in a second direction opposite to the first direction.

FIGS. 37 und 38 show an assembled configuration, wherein the bone anchoring element 1 is pivoted relative to the receiving part 500 at a maximum pivot angle $\beta_1$ to one side (FIG. 37) and a maximum pivot angle $\beta_2$ to the opposite side (FIG. 38). The maximum pivot angle is defined by the abutment of the shank 2 against the lower portion of the seat. The maximum pivot angle $\beta_1$ in FIG. 37 is larger than the maximum pivot angle $\beta_2$ in FIG. 38 because of the inclination of the first passage 51 of the receiving part 500 with respect to the second passage 56.

Modifications of this embodiment are possible. The locking ring can have any other shape that fulfills the function of compressing the head receiving portion. The surface of the five end of the projections can be flat. Alternatively, the projections can be omitted as long as the rod can engage the locking ring to move it downward. The outer surface of the first portion and the inner surface of the locking ring can have other shapes that allow for compression of the first portion by means of an increasing force when the locking ring is shifted downward relative to the receiving part.

For both embodiments, the orientation of the first longitudinal axis relative to the second longitudinal axis may be different from the orientation described before. For example, the first longitudinal axis may lie in the plane defined by the channel axis and the second longitudinal axis. The resulting pivoting of the bone anchoring element is then asymmetric in a direction along the rod axis. The first longitudinal axis may also be angled at an acute angle with respect to said plane and with respect to the channel axis.

Furthermore, the seat may be substantially symmetrical with respect to the pivoting of the head when the head pivots in any direction and the opposite direction thereof. Small cutouts at the lower edge of the seat may be present. In addition, the head and the seat may be configured to allow a symmetric pivoting in one or more discrete planes only so that the bone anchoring device has a monoplanar construction with respect to the pivot angles.

Modifications of both embodiments may further include the use of specific materials for rendering the compression member or the head receiving portion flexible. Such materials can be used instead of or additionally to providing slits.

For the bone anchoring element, various different kinds of anchoring elements can be used and combined with the receiving part. These anchoring elements may be, for example, screws with different length, screws with different diameters, cannulated screws, screws with different thread forms, nails, hooks etc. For some anchoring elements, the head and the shaft may also be separate parts that are connectable to each other.

Other kinds of locking devices including outer nuts, outer caps, bayonet locking devices, or others are also possible. Also, a two part locking device may be used wherein one part locks the head and the other part locks the rod.

It shall also be noted that portions of the different described embodiments can also be combined with each other in various different combinations.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A polyaxial bone anchoring device comprising:
a receiving part to receive a rod for coupling the rod to a bone anchoring element, the receiving part having a top end and a bottom end, a first passage at the bottom end with a first longitudinal axis, and a second passage at the top end with a second longitudinal axis that intersects the first longitudinal axis; and
a compression element;
wherein at least one of the receiving part or the compression element has a seat with an opening facing the bottom end; and
wherein the compression element is movable relative to the receiving part along the first longitudinal axis between a first position wherein the seat is expandable and configured for insertion of a head of a bone anchoring element and pivoting of the head, and a second position wherein the seat is compressed to lock an inserted head therein.

2. The polyaxial bone anchoring device of claim 1, wherein the first passage extends from the bottom end toward the top end, and the second passage extends from the top end toward the bottom end.

3. The polyaxial bone anchoring device of claim 1, wherein the first passage and the second passage are in communication with one another.

4. The polyaxial bone anchoring device of claim 1, wherein the receiving part has a channel for receiving a rod.

5. The polyaxial bone anchoring device of claim 4, wherein the channel is formed by a substantially U-shaped recess adjacent to the top end.

6. The polyaxial bone anchoring device of claim 1, wherein the seat comprises a compressible wall configured to encompass at least a portion of an inserted head of a bone anchoring element to clamp the head.

7. The polyaxial bone anchoring device of claim 1, wherein the seat has slits that are open toward the bottom end of the receiving part.

8. The polyaxial bone anchoring device of claim 1, wherein the seat has a substantially concave surface portion adapted to engage at least an outer surface portion of a head of a bone anchoring element that includes a greatest diameter of the head.

9. The polyaxial bone anchoring device of claim 1, further comprising a locking element configured to engage with the receiving part for locking a position of the receiving part with respect to at least one of a rod or a bone anchoring element.

10. The polyaxial bone anchoring device of claim 1, wherein the receiving part has a single inner surface defining both the first passage and the second passage, and wherein the seat is defined by an interior wall portion of the first passage.

11. The polyaxial bone anchoring device of claim 10, wherein the compression element comprises an outer locking ring configured to be positioned around the seat circumferentially and movable toward the bottom end of the receiving part to lock an inserted head of a bone anchoring element in the seat.

12. The polyaxial bone anchoring device of claim 1, wherein the compression element comprises a compression member configured to be positioned in the first passage of the receiving part, and wherein the seat is in the compression member.

13. The polyaxial bone anchoring device of claim 12, wherein the compression member is movable in the first passage of the receiving part, and wherein movement of the compression member toward the top end of the receiving part is restricted by a stop.

14. The polyaxial bone anchoring device of claim 12, wherein the first passage has a section with an enlarged diameter for allowing the compression member to expand therein when a head of a bone anchoring element is inserted.

15. The polyaxial bone anchoring device of claim 4, wherein the second longitudinal axis is perpendicular to a longitudinal axis of the channel.

16. The polyaxial bone anchoring device of claim 1, further comprising a bone anchoring element comprising a head and a shank, wherein the head is insertable into the seat from the bottom end.

17. The polyaxial bone anchoring device of claim 16, wherein when the head is in the seat, the head is pivotable substantially symmetrically in at least two opposite directions relative to the seat.

18. The polyaxial bone anchoring device of claim 17, wherein the head is pivotable substantially symmetrically around the first longitudinal axis.

19. The polyaxial bone anchoring device of claim 16, wherein the head has a spherical-segment shaped outer surface portion including a greatest diameter of the spherical-segment, and wherein the seat is configured to engage at least the portion of the head including the greatest diameter.

20. The polyaxial bone anchoring device of claim 16, wherein the seat is configured to cover at least a portion of the head on a side of the head opposite the shank when the head is inserted in the seat.

21. The polyaxial bone anchoring device of claim 16, wherein the receiving part comprises an opening at the bottom end with a diameter greater than a greatest diameter of the head.

22. A method of attaching a rod to a bone via a polyaxial bone anchoring device, the bone anchoring device comprising a bone anchoring element comprising a head and a shank, a receiving part having a top end and a bottom end, a first passage at the bottom end with a first longitudinal axis, and a second passage at the top end with a second longitudinal axis that intersects the first longitudinal axis, a compression element, and a locking element, wherein at least one of the receiving part or the compression element has a seat with an opening facing the bottom end, and wherein the compression element is movable relative to the receiving part along the first longitudinal axis between a first position wherein the seat is expandable and configured for insertion of the head and pivoting of the head, and a second position wherein the seat is compressed, the method comprising:
inserting the bone anchoring element into a bone;
adjusting an angular position of the receiving part relative to the bone anchoring element when the head is in the seat;
inserting a rod into a channel of the receiving part;

advancing the locking element in the channel towards the bottom end of the receiving part to advance the compression element to the second position via the rod to compress the seat and to lock an angular position of the head relative to the receiving part.

23. The method of claim 22, further comprising connecting the bone anchoring element with the receiving part prior to inserting the bone anchoring element into the bone.

24. The method of claim 22, further comprising connecting the bone anchoring element with the receiving part after inserting the bone anchoring element into the bone.

25. The method of claim 22, further comprising assembling the receiving part and the compression element.

26. The method of claim 22, wherein the locking element and the rod are advanced along the second longitudinal axis, while the compression element is advanced along the first longitudinal axis.

* * * * *